US009785750B2

(12) United States Patent
Coe et al.

(10) Patent No.: US 9,785,750 B2
(45) Date of Patent: Oct. 10, 2017

(54) MEDICINE ORGANIZER

(71) Applicant: One Word Design & Manufacturing Group LTD, Warren, NJ (US)

(72) Inventors: Matthew Coe, Annandale, NJ (US); Richard Costa, Bedminster, NJ (US); Fred Pether, New Hope, PA (US); Hung Mach, Flushing, NY (US)

(73) Assignee: ONEWORLD DESIGN & Manufacturing Group, LTD, Warren, NJ (US)

( * ) Notice: Subject to any disclaimer, the term of this patent is extended or adjusted under 35 U.S.C. 154(b) by 240 days.

(21) Appl. No.: 14/797,079

(22) Filed: Jul. 11, 2015

(65) Prior Publication Data

US 2017/0011201 A1    Jan. 12, 2017

(51) Int. Cl.
*G06F 19/00* (2011.01)
*A61J 1/18* (2006.01)

(52) U.S. Cl.
CPC ............ *G06F 19/3462* (2013.01); *A61J 1/18* (2013.01)

(58) Field of Classification Search
CPC .. G06F 19/3462; G06F 19/3456; G06F 17/00; G06F 19/3468; G06F 21/35; A61J 2200/30; A61J 7/0436; A61J 7/0418; A61J 7/0445; A61J 7/0454; A61J 2205/60; A61J 7/0084; A61J 7/0076; A61J 7/02; A61J 2205/10; A61J 7/0069; A61J 7/04; A61J 7/0409; A61J 1/1437; A61J 2200/70; A61J 7/0427; A61J 7/0463; G07F 17/0092; G07F 9/026; G07F 11/002; G07F 11/10; G06Q 50/24; G06Q 30/0267; B65D 83/0454; B65D 83/0409; A45C 15/06; A45C 2011/002; A45C 2011/003

See application file for complete search history.

(56) References Cited

U.S. PATENT DOCUMENTS

| | | | | |
|---|---|---|---|---|
| RE35,743 E * | 3/1998 | Pearson | ............... | A61G 12/001 221/123 |
| 5,790,409 A * | 8/1998 | Fedor | ...................... | G06M 7/04 700/214 |
| 6,108,588 A * | 8/2000 | McGrady | ................ | G06M 7/04 221/9 |
| 6,249,717 B1 * | 6/2001 | Nicholson | ............. | A61J 7/0481 222/246 |
| 6,259,654 B1 * | 7/2001 | de la Huerga | ........ | A61J 1/1437 368/10 |
| 6,529,446 B1 * | 3/2003 | de la Huerga | ........ | A61J 1/1437 368/10 |
| 7,048,141 B2 * | 5/2006 | Abdulhay | ............... | G07F 11/10 221/15 |
| 7,216,802 B1 * | 5/2007 | De La Huerga | .... | G06F 19/3462 235/380 |
| 7,349,858 B1 * | 3/2008 | McGrady | ............ | G06F 19/3462 705/3 |
| 8,060,249 B2 * | 11/2011 | Bear | ..................... | A61J 7/0481 700/232 |
| 8,319,613 B2 * | 11/2012 | Lazar | ....................... | A61J 1/14 340/309.16 |

(Continued)

*Primary Examiner* — Fekadeselassie Girma
(74) *Attorney, Agent, or Firm* — Mitchell J. Mehlman, Esq.

(57) ABSTRACT

Medicine organizers and methods comprising integrated elements using smart wireless devices to provide assistance to individuals in order to organize or monitor the administration of one or more medications are provided.

6 Claims, 16 Drawing Sheets

(56) References Cited

U.S. PATENT DOCUMENTS

| | | | | |
|---|---|---|---|---|
| 8,407,063 B2* | 3/2013 | Brown | A61B 5/0002 | 705/2 |
| 8,423,180 B1* | 4/2013 | Frederick | G06Q 10/087 | 700/236 |
| 8,652,043 B2* | 2/2014 | Drucker | A61B 5/0002 | 600/309 |
| 8,708,192 B2* | 4/2014 | Flowers | A61J 7/0409 | 221/2 |
| 8,950,223 B1* | 2/2015 | Joyce | A45C 11/321 | 439/134 |
| 9,027,787 B2* | 5/2015 | Eriksson | A61J 7/0481 | 221/120 |
| 9,211,233 B2* | 12/2015 | Shavelsky | A61J 7/04 | |
| 9,439,835 B2* | 9/2016 | DiMartino | A61J 7/0076 | |
| 9,498,408 B2* | 11/2016 | Lehmann | G06F 19/3462 | |
| 9,539,177 B2* | 1/2017 | Solvell | A61J 7/0076 | |
| 9,563,600 B2* | 2/2017 | Rothschild | A61J 1/03 | |
| 2003/0086338 A1* | 5/2003 | Sastry | G06F 19/3462 | 368/10 |
| 2004/0129716 A1* | 7/2004 | Naufel | G07F 11/62 | 221/9 |
| 2008/0119958 A1* | 5/2008 | Bear | A61J 7/0481 | 700/244 |
| 2009/0192648 A1* | 7/2009 | Namineni | A61J 7/0481 | 700/231 |
| 2009/0281657 A1* | 11/2009 | Gak | A61J 7/0481 | 700/242 |
| 2010/0096399 A1* | 4/2010 | Ratnakar | A61J 7/02 | 221/1 |
| 2010/0100237 A1* | 4/2010 | Ratnakar | A61J 7/02 | 700/232 |
| 2010/0318218 A1* | 12/2010 | Muncy, Jr. | G06F 19/3462 | 700/220 |
| 2012/0006847 A1* | 1/2012 | Coe | A61J 7/0481 | 222/52 |
| 2012/0102894 A1* | 5/2012 | TerHaar | B65D 43/16 | 53/492 |
| 2012/0187142 A1* | 7/2012 | Flowers | G07F 17/0092 | 221/7 |
| 2012/0265545 A1* | 10/2012 | Hwang | G06F 19/3456 | 705/1.1 |
| 2012/0265548 A1* | 10/2012 | Hwang | G06Q 30/0207 | 705/2 |
| 2013/0027183 A1* | 1/2013 | Wu | G07F 15/006 | 340/5.64 |
| 2013/0151005 A1* | 6/2013 | Gerold | G06F 19/3462 | 700/235 |
| 2013/0304255 A1* | 11/2013 | Ratnakar | G07F 9/02 | 700/242 |
| 2013/0307683 A1* | 11/2013 | Greenberg | A47G 19/2227 | 340/539.1 |
| 2014/0285335 A1* | 9/2014 | Haas | G08B 21/24 | 340/500 |
| 2014/0372144 A1* | 12/2014 | Sterns | G06F 19/3418 | 705/2 |
| 2015/0232256 A1* | 8/2015 | Hoover | A61J 7/0069 | 700/236 |
| 2015/0283036 A1* | 10/2015 | Aggarwal | A61J 7/04 | 206/534 |
| 2016/0034669 A1* | 2/2016 | Mahbubian | G06F 19/3462 | 700/232 |
| 2016/0158107 A1* | 6/2016 | Dvorak | A61J 7/0084 | 241/25 |
| 2016/0287480 A1* | 10/2016 | Hancock | A61J 7/02 | |
| 2016/0328535 A1* | 11/2016 | Barr | G06F 19/3456 | |

* cited by examiner

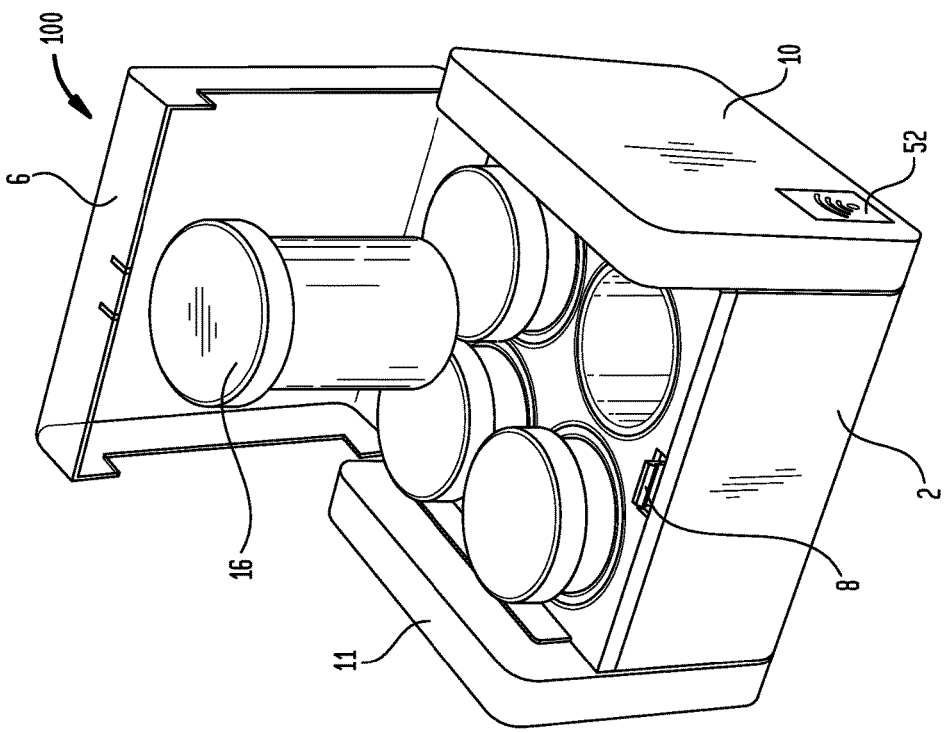
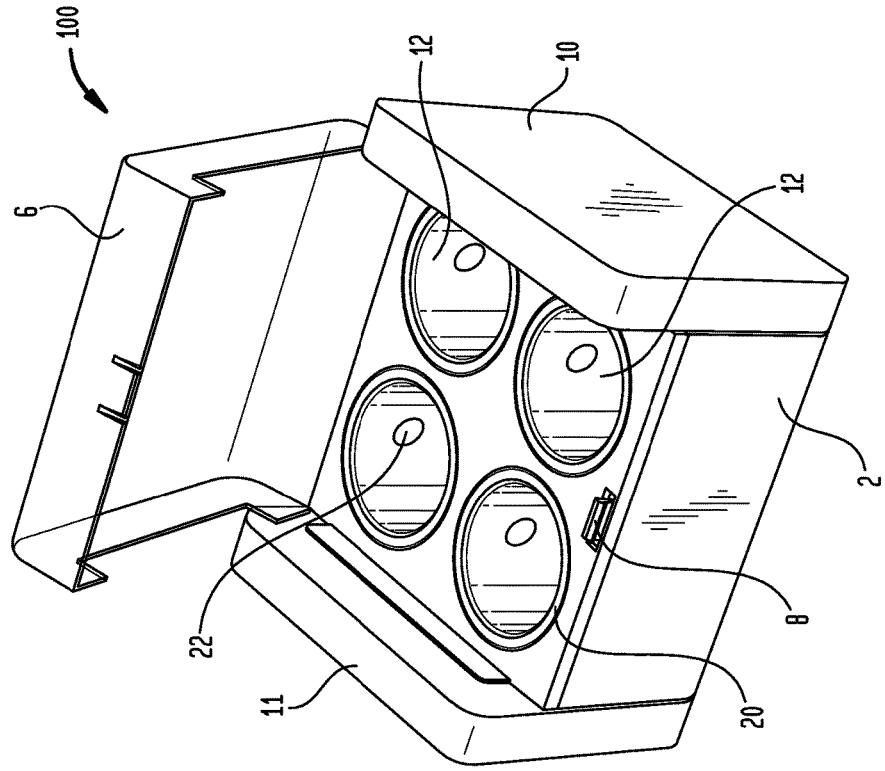

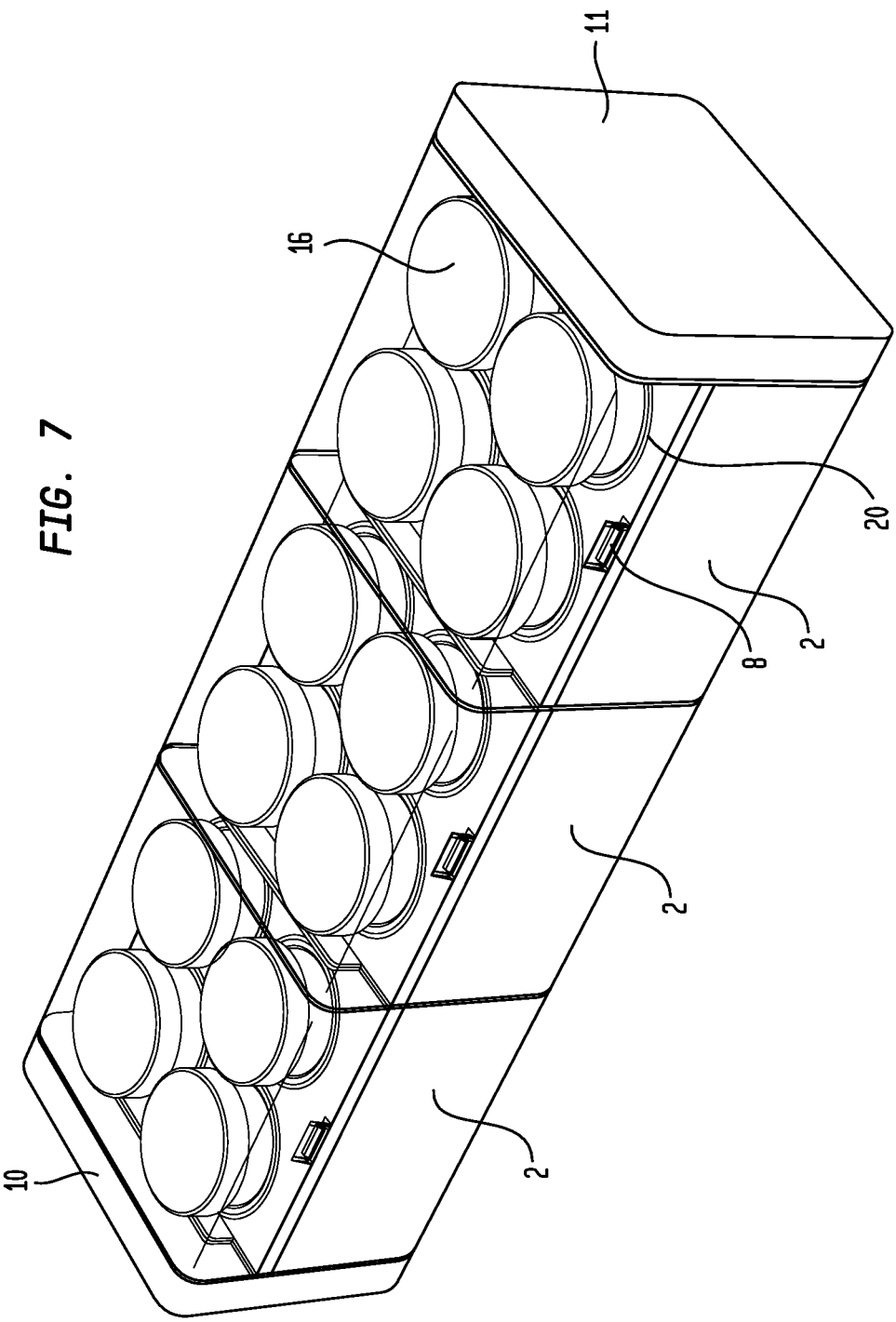

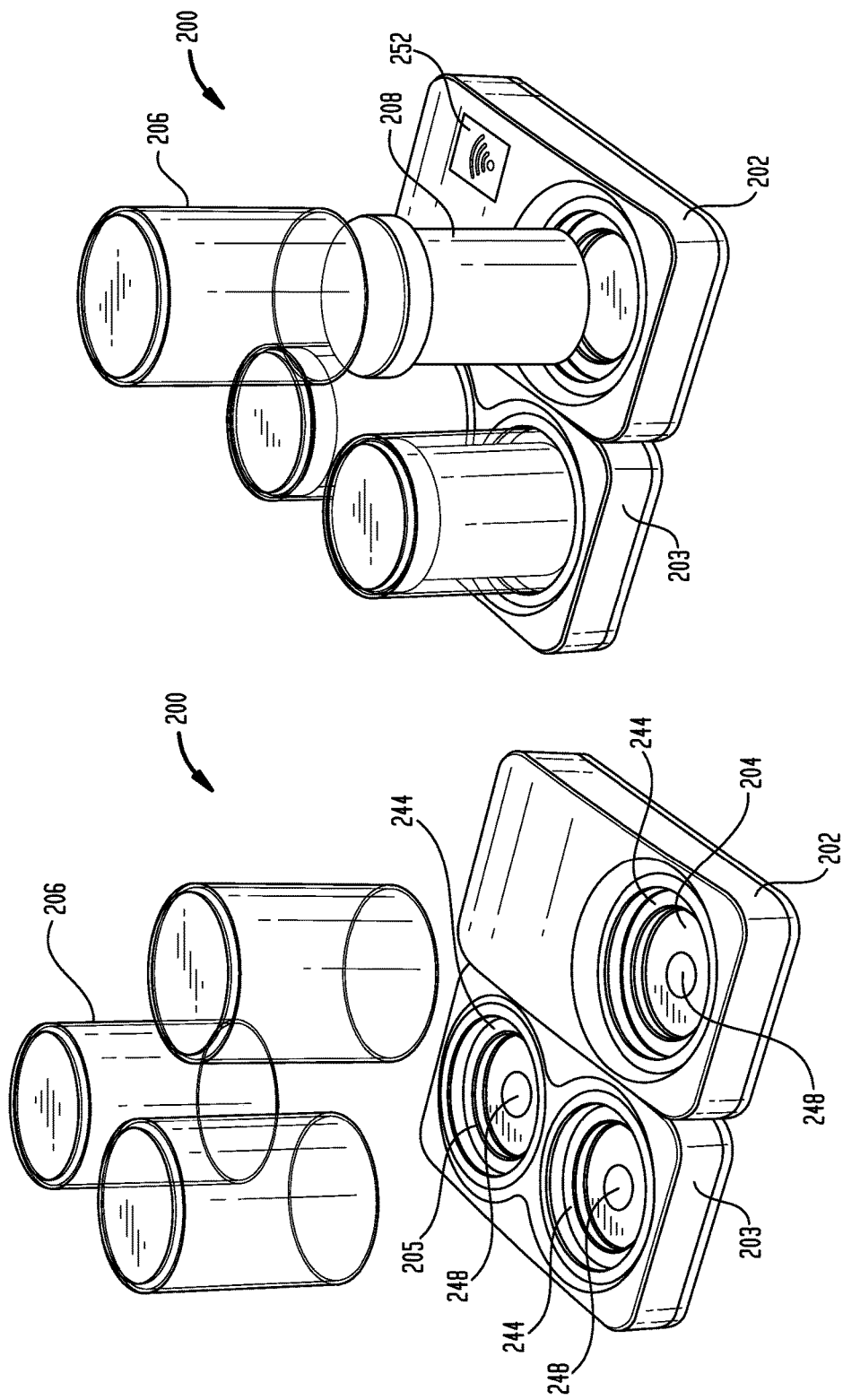

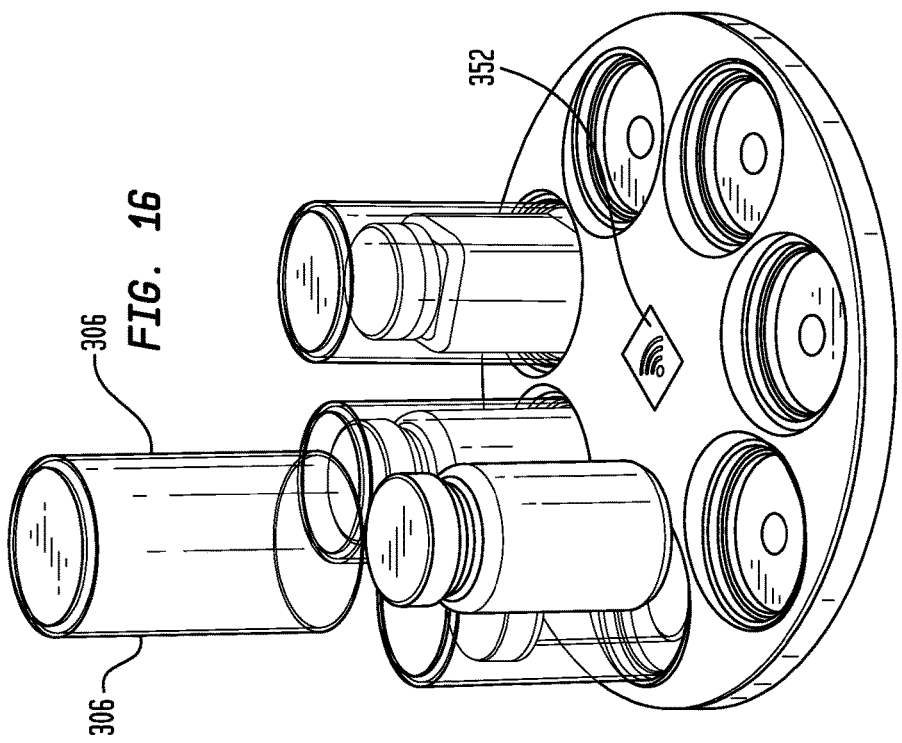
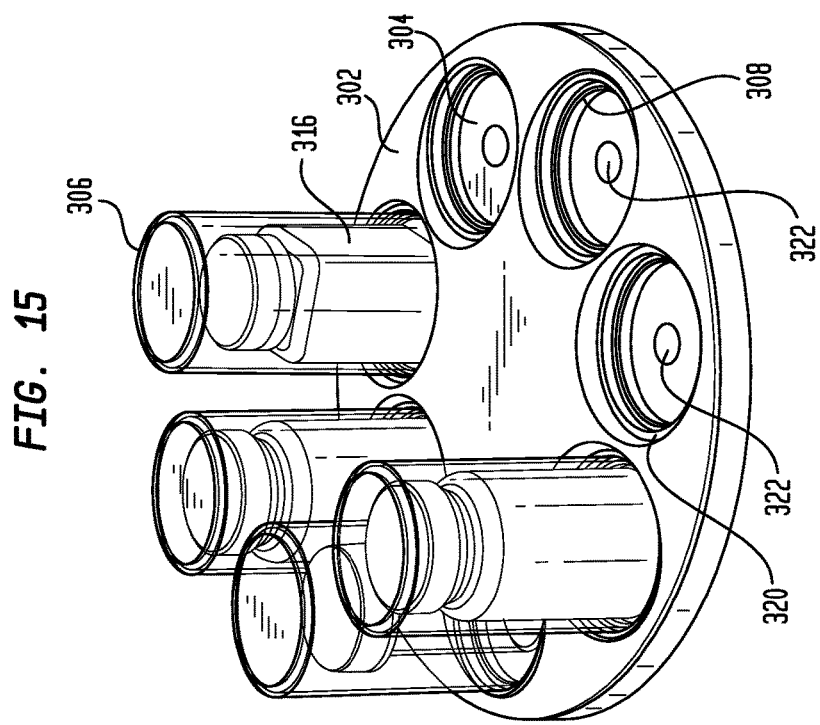

MEDICINE SCHEDULE SCREEN.

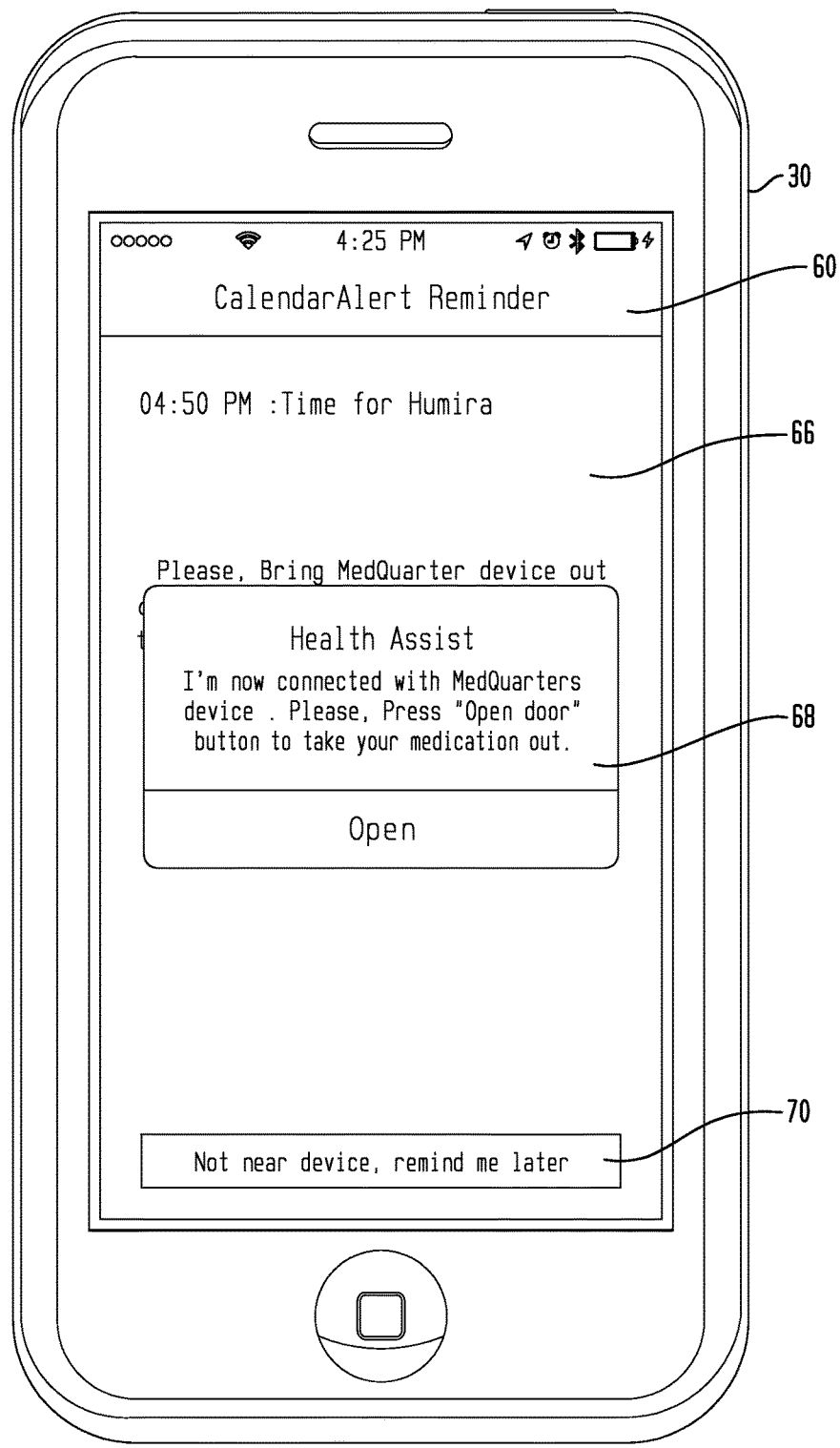

ADHERENCE TRACKING

ADHERENCE TRACKING

ADHERENCE TRACKING

MEDICINE ORGANIZER

BACKGROUND OF THE INVENTION

The present invention relates to medicine organizers and modular systems, including smart wireless devices such as smart phones or tablets that can communicate with one or more medicine storage devices and methods for monitoring and increasing patient compliance with regard to timely and accurate dispensing of medicines.

Many people take one or more medicine or supplements, such as minerals or vitamins, several times a day to maintain or improve their health. Often, these medications or supplements must be taken at specific times each day. If medications or supplements are not taken at the proper times, individual health may be jeopardized. For example, failure to take a prescribed medication for treatment of heart disease can result in severe health consequences such as a heart attack or stroke. Similarly, patients that seek to take extra doses before the prescribed time interval can be in danger of an overdose. Non-compliance with a prescribed dose regimen includes patients who fail to take a dose at a prescribed time or patients who take one or more extra doses that are not in compliance with the minimum time between dose of the particular prescription or label instructions for ingestion.

Further, non-compliance with a prescribed regimen of one or more medications, particularly in the elderly and the aging population of "baby boomers", can result in billions of dollars of unnecessary health care costs.

Many people who take one or more medication or supplement a day are able to take medications or supplements without assistance. However, many people who take one or more medication or supplement a day require a reminder or the assistance of a care taker. Care takers may be one or more members of the patient's family or other individuals, such as friends, nurses, nurse's aids and the like. It can be difficult for a patient or a care taker to organize a patient's medications or supplements to insure compliance with a predetermined schedule. Further, it can be extremely difficult to monitor compliance with multiple medication schedules. Failure to properly monitor compliance can result in catastrophic health consequences to the patient and high levels of care taker anxiety, which can also lead to increased health problems for care givers.

The present invention provides novel methods and structures for improving the overall ease of compliance with a programmable schedule for reminding a patient to take one or more medications or supplements.

Improved medicine organizers comprising smart wireless devices such as smart phones and tablets having programmable software that can communicate with one or more medicine dispenser and methods for monitoring and improving patient compliance with medication schedules are disclosed herein.

SUMMARY OF THE INVENTION

In one aspect of the invention an apparatus comprises a module having a housing, a first end cap, a second end cap, and at least one compartment configured for storing a medicine vial. The module can include a lockable lid. At least once sensor can be located within the compartment. The sensor can be configured to detect the presence of the medicine vial in the compartment. At least one light is capable of being commanded to an illuminated condition to illuminate the compartment at a predetermined medication time. A wireless controller can be connected to the first end cap. The controller can send signals to open or lock the lockable lid and to illuminate the light. A smart device is capable of commanding the controller to open the lid and illuminate the light at a predetermined medication time. The smart device can execute a software application for alerting a user at a predetermined medication time based on a data set input by a user.

In one embodiment of this aspect, the smart device can be a smart phone.

In another embodiment of this aspect, the housing can include four compartments.

In some embodiments of this aspect the light can be a LED (light emitting diode).

In certain embodiments, the sensor can be an optical sensor.

In some embodiments of this aspect the wireless controller can utilize a blue-tooth wireless protocol for pairing with the smart device.

In certain embodiments, the data set can include a name of a medicine; a strength of the medicine; and a time schedule for dispensing the medicine.

In a particular embodiment of this aspect, the apparatus can include a plurality of modules. The plurality of modules can be electrically interconnected and configured to be assembled together between the first end cap and the second end cap. The wireless controller is capable of controlling the each of the lockable lids and each of the lights in each of the plurality of modules.

In another aspect of the present invention, an apparatus includes a module having a housing, a compartment, a locking mechanism, and a removable lockable lid. A sensor can be located within the compartment, the sensor being configured to detect the presence of a vial in the compartment. A light can be located to illuminate the compartment. The light can be commanded to an illuminated condition at a predetermined medication time to alert a user of which medicine vial in which compartment to access and use. A wireless controller can be connected to the housing. The controller can command the locking mechanism to open or to lock the lockable lid and to illuminate the light on one or more compartments in a specific pre-determined order. A smart device can command the controller to open the lid and to illuminate the light at any predetermined medication time. The smart device can be wirelessly paired with the wireless controller and can execute a software application for alerting a user at a predetermined time based on a data set input by any user.

In some embodiments of this aspect, the lid can be commanded to an open position and the light can be illuminated only when the smart device is wirelessly paired with the wireless controller.

In certain embodiments, the housing can comprise two compartments.

In some embodiments, the light can be an LED ring or other LED configuration sufficient to illuminate any compartment where a medicine is stored at the predetermined dispensing time.

In certain embodiments, the sensor can be an optical sensor.

In several embodiments, the wireless controller can utilize a blue-tooth wireless protocol for pairing with a smart device.

In certain embodiments of this aspect, the data set can include the name of a medicine; the strength of the medicine; and a time schedule for dispensing the medicine.

In a particular modular embodiment, a plurality of dumb modules (i.e. no controller is present in a "dumb" module)

can be configured to include a housing, a compartment, a locking mechanism, a sensor, a light and a removable lockable lid. The plurality of dumb modules can be assembled together and connected to the ("smart") module (i.e. the module including the wireless controller, power and associated power and control hardware) thereby providing power and control functions to the plurality of dumb modules.

In another aspect of the invention an apparatus can include a housing. The housing can have at least one compartment, at least one locking mechanism corresponding with the at least one compartment, and at least one removable lockable lid corresponding with the at least one compartment. At least one sensor can be configured to detect the presence of at least one vial in the at least one compartment. At least one light can be commanded to an illuminated condition at a predetermined medication time to alert a user of the time and the location of the medicine to be taken. A controller can be connected to the housing. The controller can command the at least one locking mechanism to open or to lock the at least one lockable lid and to illuminate or to de-illuminate the at least one light. A smart device is capable of wirelessly commanding the controller to open the at least one lid and to illuminate the at least one light at the predetermined medication time. The smart device can be wirelessly paired with the controller and can execute a software application for alerting a user at any predetermined medication time based on a data set input by a user.

In some embodiments of this aspect, the housing can be circular.

In certain embodiments, the at least one light can be an LED light or ring of lights configured to illuminate the compartment.

In some embodiments, the at least one sensor can be an optical sensor.

In other embodiments, the controller can utilize a bluetooth wireless protocol for pairing with the smart device.

In another aspect of the instant invention, a method for administration of medicine can include the steps of 1) entering a data set into a software application, the application can be executed on a smart wireless device 2) commanding a lid to an open or unlocked position 3) loading a medicine vial into a compartment, the compartment including a light 4) commanding the lid to a closed or locked position 5) receiving an alert from the smart wireless device 6) commanding the lid to an open or unlocked position and 7) commanding the light to an illuminated condition, thereby alerting a user that it is time to take a medicine.

In one embodiment of this aspect, the method can include the step of transmitting a signal from the smart device to a remote database. The signal can indicate either a confirmation of dispensing the medicine or a failure to dispense the medicine.

In another embodiment, the method can include the step of transmitting one or more alarms from the smart device when the medicine is not dispensed within a predetermined time of a scheduled pre-determined dispensing time.

In some embodiments, the method comprises the step of sending a signal to a remote database when a user attempts to dispense a medicine before a predetermined time.

BRIEF DESCRIPTION OF THE DRAWINGS

FIG. 1 is an isometric view of a medicine organizer according to one embodiment of the present invention in an open position.

FIG. 2 is an isometric view of some of the elements included in the medicine organizer of FIG. 1 depicting several stored medicine vials.

FIG. 7 is an isometric view of some of the elements included in the medicine organizer of FIG. 6 showing an assembled modular structure.

FIG. 8 is an isometric view of a medicine organizer according to one non-limiting embodiment of the present invention.

FIG. 9 is an isometric view isometric view of some of the elements included in the medicine organizer of FIG. 8.

FIG. 15 is an isometric view of some of the elements included in the medicine organizer of FIG. 13 in a modular configuration.

FIG. 16 is an isometric view of some of the elements included in the medicine organizer of FIG. 13 in a modular configuration.

FIG. 18B depicts a reminder screen on a smart device application according to several embodiments of the invention.

DETAILED DESCRIPTION

Figure 3:
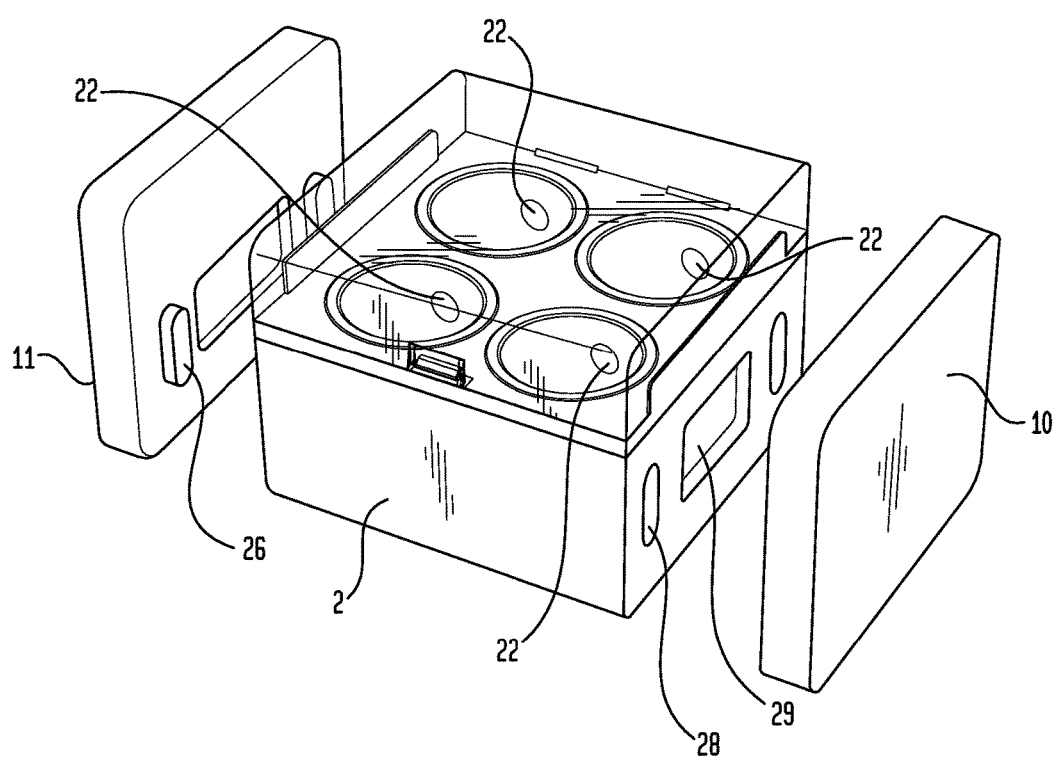
FIG. 3 is an isometric exploded view of some of the elements included in the medicine organizer of FIG. 1.
Figure 4:
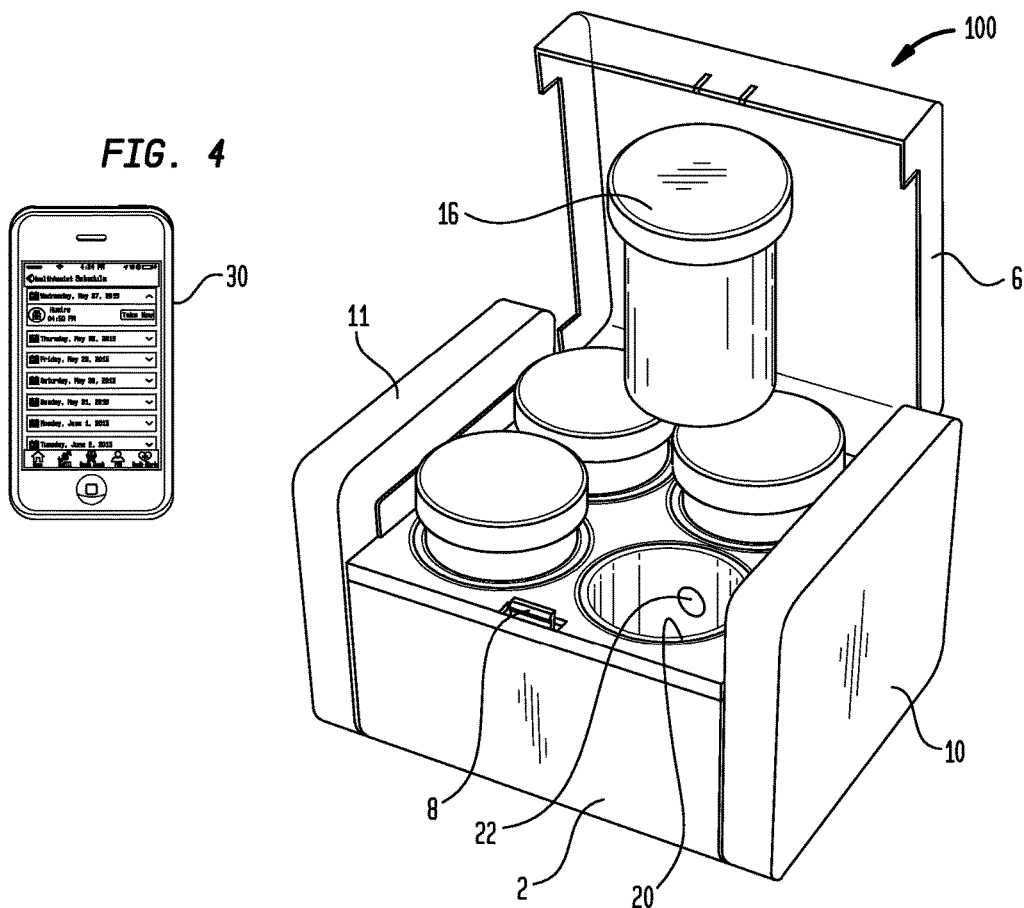
FIG. 4 is an isometric view of some of the elements included in the medicine organizer of FIG. 1 showing the lid in an open position.
Figure 5:
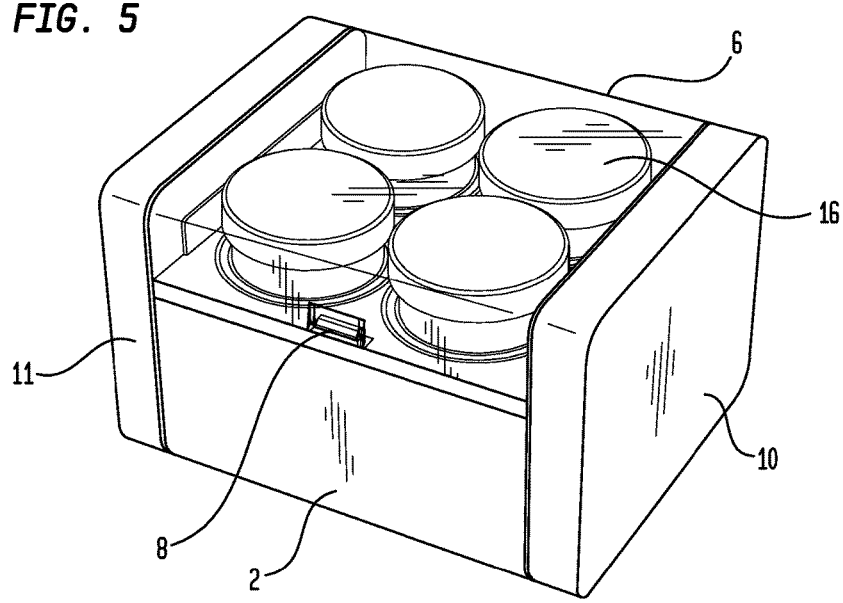
FIG. 5 is an isometric view of some of the elements included in the medicine organizer of FIG. 1 showing the lid in a closed position.

As used herein, the terms medicine, pill and pills refer to any size or shape of a capsule, caplet, granule, tablet, lozenge, suppository, ampoule or any other dosage form typically used for oral nasal, dermal or rectal administration of a medication or dietary supplement or for rectal administration in the form of a suppository. The term pill or pills can include medications used for injections. The terms pill and pills may also include delivery forms typically used for topical administration, such as encapsulated and packaged liquid suspensions or emulsions, powders, creams, salves, serums, ointments and the like. The terms pill, medicine or medication may be singular or plural and are used interchangeably herein.

As used herein, the terms pill, medicine and or medication refer to prescription and over-the-counter medications, dietary supplements such as vitamins, minerals or cosmetic products. Further, the terms pill, medicine and or medication refer to any product in pill form which the user has a need or desire to use on a predetermined, scheduled basis. Further, the terms medicine and medicines can refer to any product which the user has a need or desire to use on a predetermined, scheduled basis.

As used herein, the terms bluetooth, wireless, wireless communication or wireless protocol includes bluetooth, Wi-Fi and other known or future methods for secure wireless protocol that use electromagnetic radiation to connect wireless-enabled computers and devices to each other. Bluetooth simplifies communications between bluetooth-enabled computers and devices by creating personal area networks (PANs). To create a bluetooth PAN, a user must have at least two devices that contain bluetooth electronics. A person of ordinary skill in the art will understand that a variety of known or future wireless command, control, and data systems can be used in the instant invention.

The operating range for a given device depends on the device class. One type is primarily used in computers and mobile devices, such as cell phones, PDAs, or MP3 players. The operating range is about 30 feet (10 meters). Not all wireless or bluetooth interfaces are the same. There are different versions of drivers with different interfaces as will be understood by a skilled artisan.

Bluetooth is only one standard wire-replacement communications protocol primarily designed for low-power consumption, with a short range based on low-cost transceiver microchips in each device. Because the devices use a radio (broadcast) communications system, they do not have to be in visual line of sight of each other, however a quasi-optical wireless path must be viable. A person of ordinary skill in the art of electronics will understand how to implement a wireless protocol such as blue tooth or Wi-Fi communication protocol between a storage container for injectable medicines and a smart phone or other wireless device designed to communicate with a medicine storage container.

As used herein the term "smart phone" or "smart device" includes any device capable of wireless command, control, and data management including but not limited to phones, tablets, lap-tops, computers, and other devices which can run software applications and utilize known or future wireless communication protocols to communicate with a remote device.

In one non-limiting embodiment of the present invention as shown in FIGS. 1-7, device 100 includes a housing 2 and a lid 6 being lockable to the housing to form a closed or an open unit. The device can use a battery to provide power. Alternatively, a hardline power source can also be used. The lid is preferably transparent or translucent.

The housing 2 includes a commandable locking mechanism 8 to lock the lid of housing until a medication dose is scheduled to be taken. The locking mechanism is operated by a smart device application as discussed below using a wireless communication protocol and a smart device. When the pre-determined time set in the application occurs, and the smart device is in wireless proximity with a wireless electronic communication module connected to smart end cap 10, the device and the smart phone are "paired", thus enabling the lock to open and allow a user access to the medicine via by opening the lid. A signal from the smart phone via a wireless protocol will enable a mechanical device such as a solenoid, actuator, or magnet to open or close the lock (not shown). A "dumb" or protective end cap 11 can seal one side of the housing and be used as an protective end cap in a modular arrangement as discussed below. A person of ordinary skill in the electro-mechanical arts will understand that the proximity locking and unlocking function can be carried out in a number of known ways.

The housing includes compartments 12 for storing medicine vials 16. The compartments can include a light 20 for each compartment, such as, for example an LED light, or an illuminated area which can illuminate, change color, or flash when it is time to take a medication stored inside the compartment, when the device malfunctions, when the device is paired to a smart phone, or when the device is low on power.

In some embodiments, housing can include a by-pass switch to allow a user to unlock the lid in case of emergency or malfunction and to allow access to the contents of the housing. The use of the by-pass switch can be electronically recorded and sent to the smart phone application for review and analysis.

In this embodiment, housing 2 can include a switch or sensor for sensing when the lid is opened or closed. The switch can be, for example, an electrical switch, a mechanical switch, an optical switch, or other type of sensor 22.

The housing 2 also includes smart end cap 10 for housing wireless transceiver or chip set 52 and associated hardware necessary to carry out the wireless command and control function and to communicate information to the smart device and the application residing on the device. Information regarding the status of the lid, including when it is opened and closed, or how many times it opened or closed, can be transmitted to the smart device and utilized by the application to provide user data.

In this embodiment, sensors 22 located within the compartments can be used to sense when a vial is in the compartment. The sensor can send position data via the wireless connection protocol to the smart device which can be utilized by the application to provide user data. Designated compartments will illuminate when it is time to take this medicine stored in the corresponding compartment. Once the vial is removed from the compartment, the illumination with automatically shut off after the vial has been removed and replaced into its compartment. After dosing, the vials are replaced in the device, the lid is closed and locked and the dosing program continues according to the preprogrammed application.

In use, a user installs custom software application on a smart device such as smart phone 30. After the application "pairs" the smart device with wireless chip set or wireless transceiver 52 which can be located within the smart end cap, the lock can be disengaged and the user can open the lid.

Next, the user can load medicine vials or other medicines into the compartments of the housing and close the lid to lock the contents inside the housing and start a dosing regimen.

In this embodiment, the application can be programmed to send the user an alarm on the smart phone and illuminate the light(s) in the appropriate compartments at pre-determined times.

When the user next approaches the device, (i.e. the smart device and housing will remain "paired" and will connect wirelessly when the phone is in range of the housing) the smart phone application can be used to open the locking mechanism by sending a wireless signal to actuate the locking mechanism. The user can now access the medicine vials stored in the device.

When the user accesses the medicine, the sensor 22 can electronically time stamp each time the lid is opened or closed. This data can be sent to the smart phone application for review and analysis. After each use, the lid is closed and locked. A timer in the application restarted so that when the next dose is due, the process is repeated.

Referring to FIGS. 18A-18B and 19A-19C, in one embodiment, the smart device application 60 includes a scheduling screen 62. When a medicine is due, the user will receive a visual or audible prompt 64. As the user approaches the device 100 with the paired smartphone, the application can display a reminder screen 66 (FIG. 18B) in order to prompt the user to open the device 68 or to snooze until a later time 70 when the user wants to take the medicine.

Figure 19A:
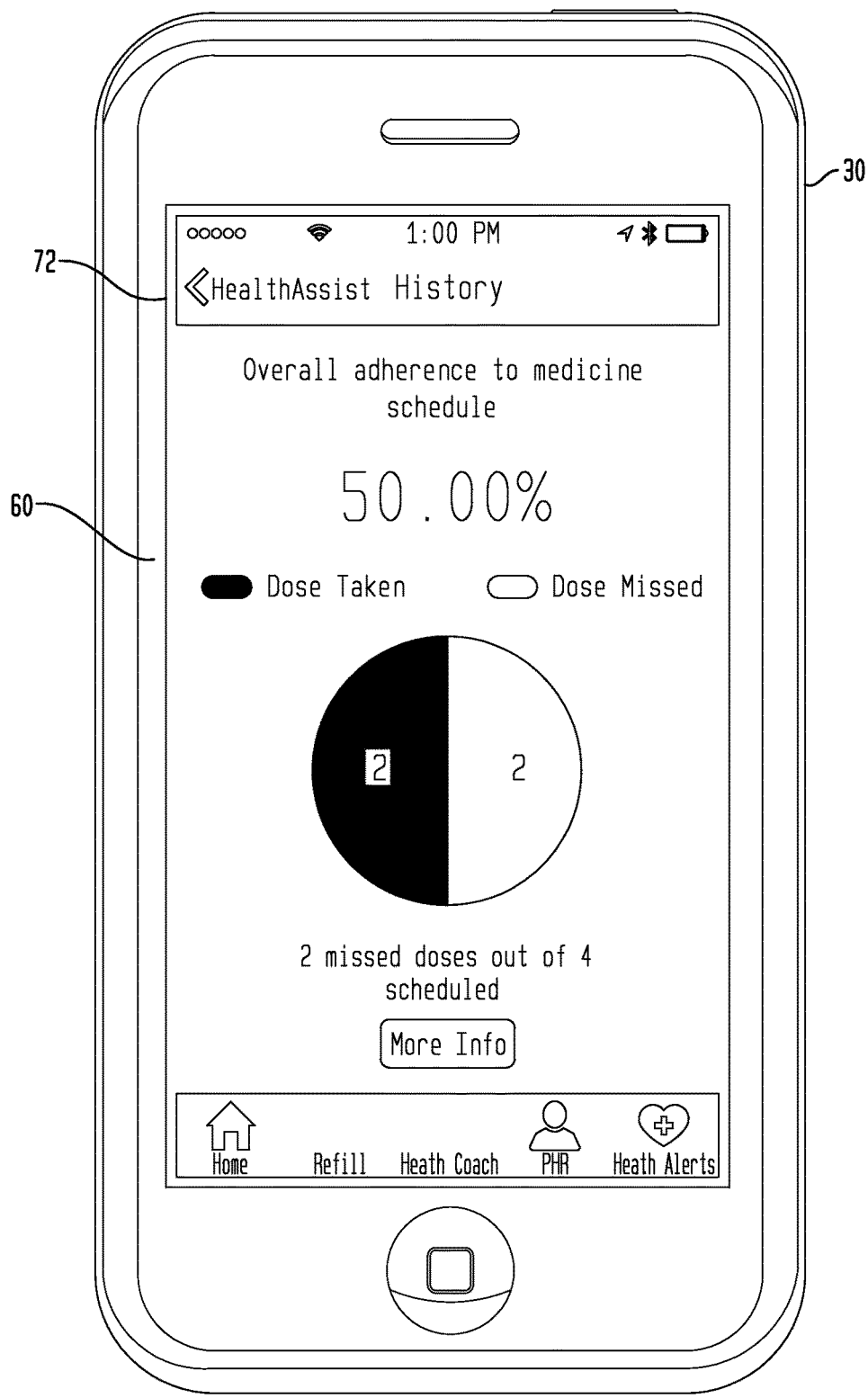
FIGS. 19A-19C depict various screens on a smart device application that can be used for adherence tracking according to several embodiments of the invention.
Figure 19B:
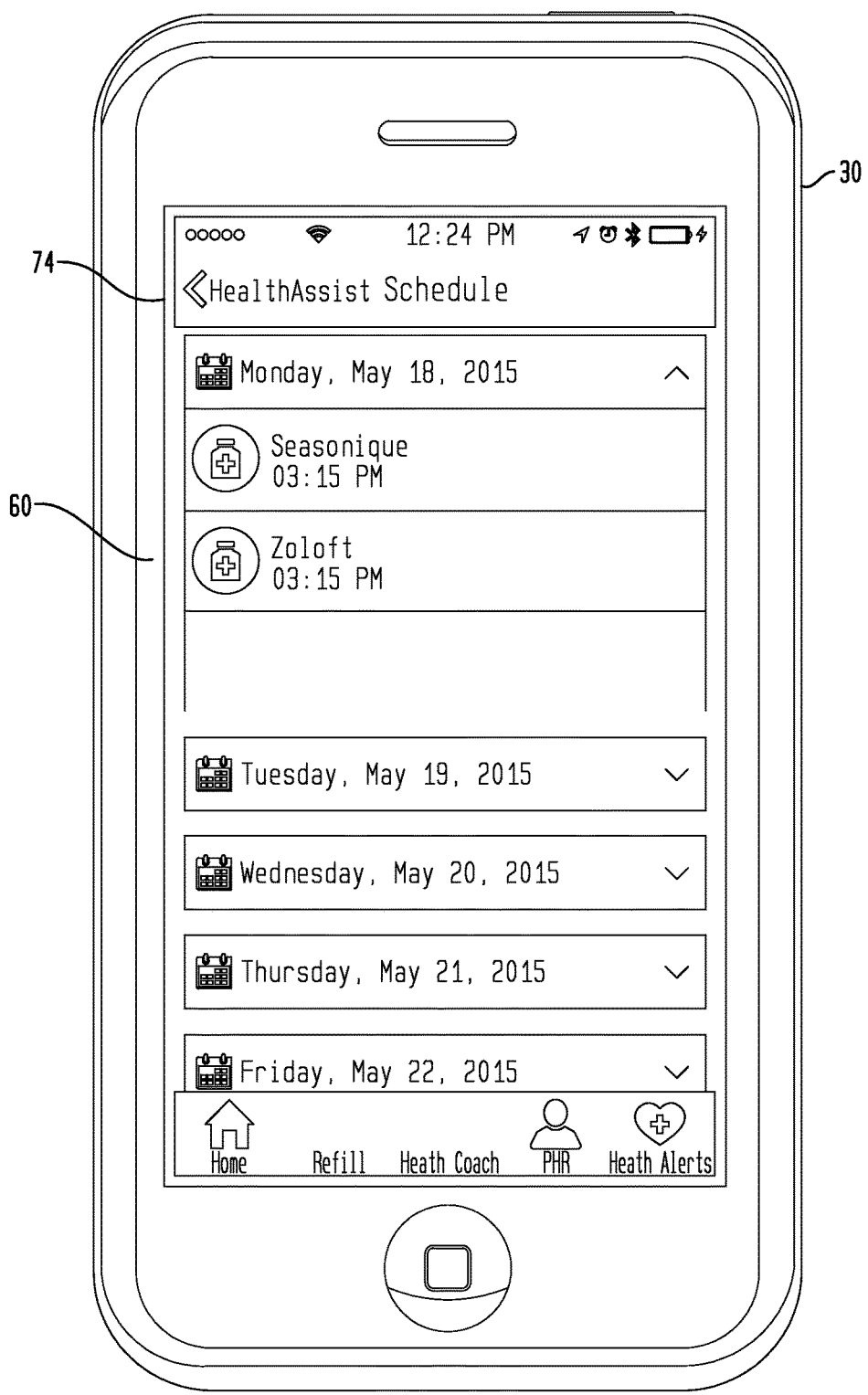
Figure 19C:
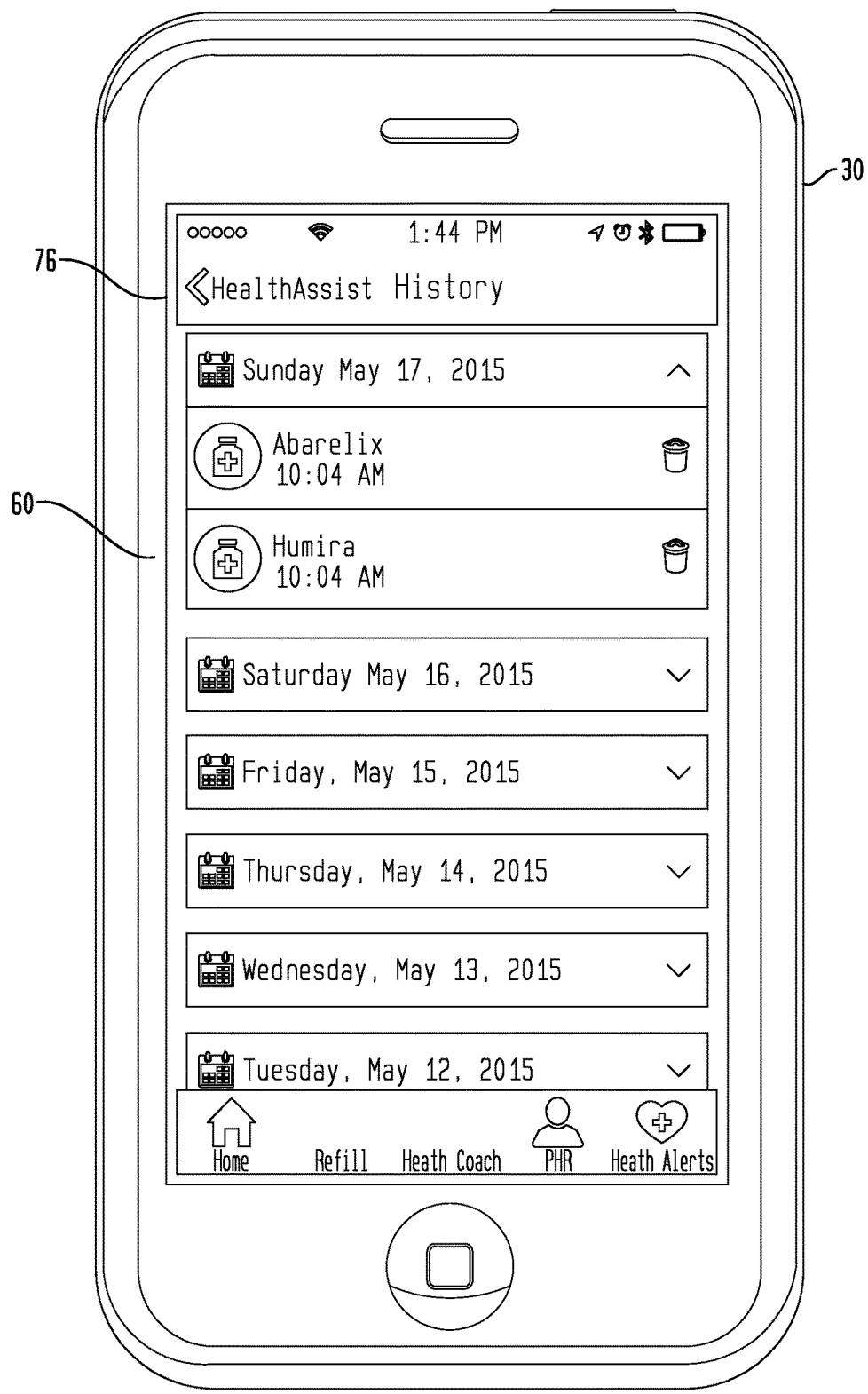

Referring to FIGS. 19A-19C, three example screens of application 60 are shown. Screen 72 depicts an adherence chart indicating the overall patient compliance to the medicine schedule. Screen 74 depicts a schedule screen that shows the user which medicines are due, the time and the date due. Screen 76 depicts the history of when the medicine was taken so that a user may review the prior dosing history.

In some embodiments, the housing can include a battery or a rechargeable battery (not shown). Optionally, the housing can be powered by an external power source, through power port 27, such as by a plug and power outlet and can include a backup battery in case of power failure.

Figure 6:
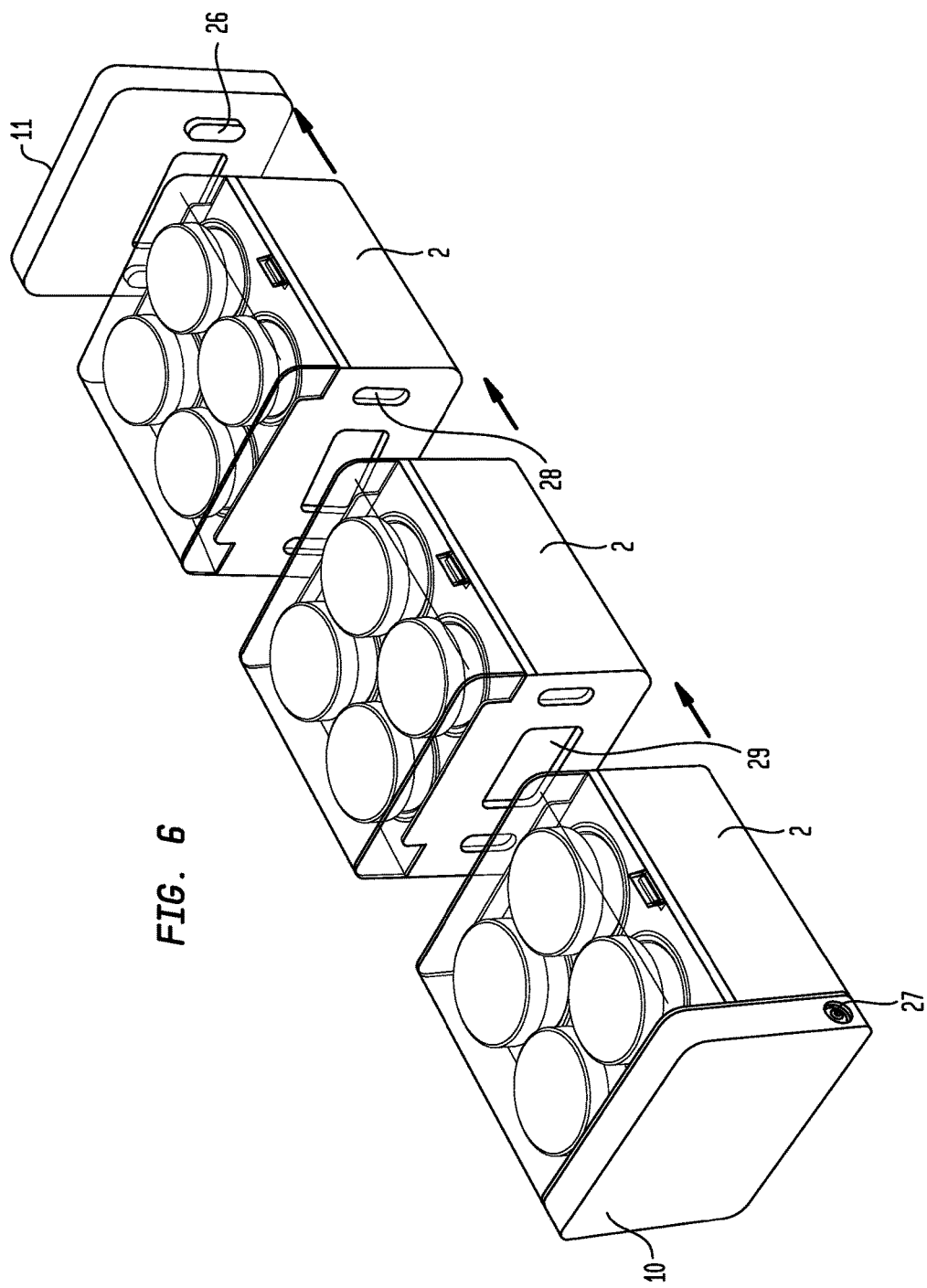
FIG. 6 is an isometric view of some of the elements included in the medicine organizer of FIG. 1 showing a modular structure that can be assembled.
Figure 11:
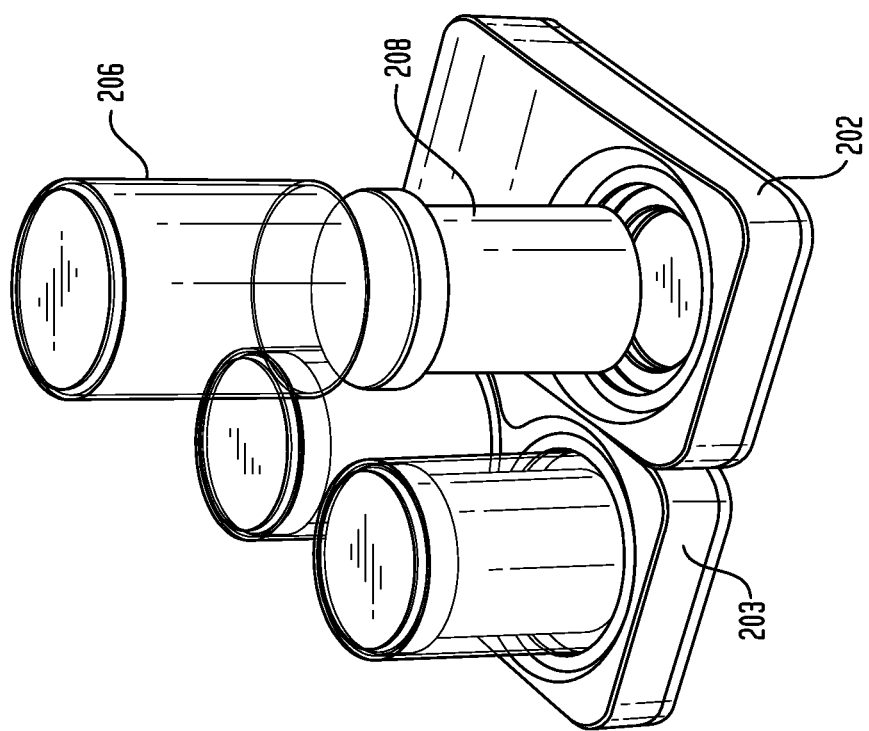
FIG. 11 is an isometric view of some of the elements included in the medicine organizer of FIG. 8.
Figure 10:
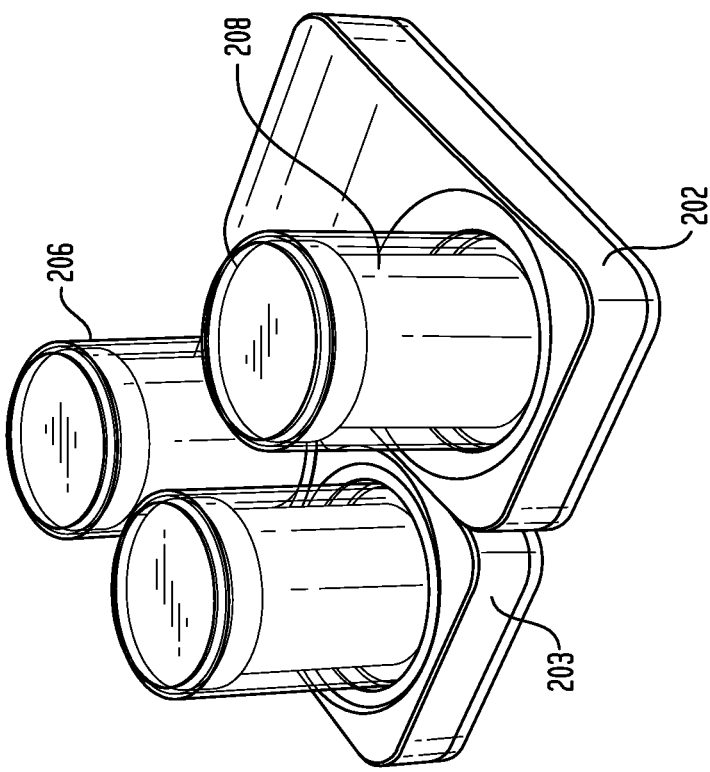
FIG. 10 is an isometric view of some of the elements included in the medicine organizer of FIG. 8.

As shown in FIGS. 6-7, the device can be a modular configuration having a plurality of housings that can fit together via interlocking features 26 and 28 on the end caps 10, 11 to allow for additional capacity. It is important to consider that the modular configuration requires a smart end cap on the "smart" unit to provide electronic signals to all of the "dumb" units. A dumb or protective endcap 11 is included on the last unit of the modular assembly. The interlocking features 26, 28, 29, are used to hold the assembly together in a module that can be assembled or disassembled easily and to provide power and electronic signals for sending and receiving data from the electronics in the smart end cap to the sensors in the "dumb" units, for example, to illuminate a compartment, unlock or lock a lid, or signal that a lid is open or closed.

The structure of the device can be fabricated from plastics or other structural materials and molding or fabrication processes which will be known to one skilled in the art of manufacturing.

In another non-limiting embodiment of the present invention as shown in FIGS. 8-12, device 200 includes a housing 202 and at least one compartment 204 being recessed in the housing. The housing 202 can include a battery (not shown) located within the housing. The battery can be used to provide power to the device.

The device includes transparent or translucent lids 206 for covering medicine vials 208. The device is operated by a smart phone application 60 using a wireless communication protocol and a smart phone as discussed above. When the pre-determined time set in the application occurs, and the smart phone is in proximity with a wireless electronic communication module 252 which can be located in the housing, when the smart phone is "paired", a signal can be sent enabling the light(s) to illuminate and allow a user access to the medicine by opening the lid(s). A person of ordinary skill in the electro-mechanical arts will understand that the locking and unlocking function can be carried out in a number of known ways.

The housing 202 can include a light ring or other light 244, such as, for example an LED light, or an illuminated area which can illuminate, change color, or flash when it is time to take a medication stored inside the housing, when the device malfunctions, when the device is paired to a smart phone, or when the device is low on power.

In this embodiment, housing 202 includes sensor 248 for sensing when the lid is open or closed. The sensor 248 can be, for example, an electrical switch, a mechanical switch, or an optical switch or other sensor.

The housing 202 can also include a wireless electronic communication module 252 and associated hardware necessary to carry out the wireless command and control function and to communicate information to the smart phone and the application residing on the phone. Information regarding the status of the lid, including when it is opened and closed, or how many times it opened or closed, can be transmitted to the smart phone and utilized by the application to provide user data.

In use, as discussed above, a user installs a custom software application 60 on a smart phone (See FIGS. 18-19). After the application "pairs" the smart phone with a wireless chip set or wireless transceiver 252 in the housing, the lid(s) are opened by the user.

Next, the user can load vials 208 or other medicines into the compartments 204 and replace the lid(s) and start a dosing regimen. As discussed above, a commandable locking mechanism 205 can be used to lock the lids in place for security.

In this embodiment, the application can be programmed to send the user an alarm on the smart phone and illuminate the light(s) 244 at pre-determined times.

When the user approaches the device, (i.e. the smart phone and device will remain "paired" and will connect wirelessly when the phone is in range of the housing) the smart phone application can be used to open the locking mechanism, by sending a wireless signal to actuate the locking mechanism. The user can now access the medicine vial 208 stored in the device 200.

When the user accesses the medicine, the sensors 248 can electronically time stamp each time the lid is opened or closed. Further, each sensor 248 can be configured to detect the presence or the absence of a medicine vial 208 within each compartment 204.

Access data, such as when the lid was removed and replaced for each compartment, can be sent to the smart phone application for review and analysis. After each use, the lid is closed and can be locked. A timer in the application is restarted so that when the next dose is due, the process is repeated.

In some embodiments, the housing includes a battery or a rechargeable battery. Optionally, the housing can be powered by an external power source, such as by a plug and power outlet and can include a backup battery.

In one embodiment, the housing or drawer can include a light sensor to determine whether the housing is in a lighted place or in a dark place. If, for example, if the housing is kept in a dark refrigerator, the sensor can signal the device to enter a "sleep mode" thereby saving power and extending the life of the battery. When the refrigerator is opened and ambient light is detected by the sensor, the device will enter a "wake" mode to perform its required functions as discussed above.

In this embodiment, as discussed further below, the housings can be configured to be a modular expandable system. For example, as shown in FIGS. 8-12 the "smart" electronics 252 can be located in one housing 202, while one or more modular expandable housings 203 are used to expand the configuration.

Figure 12:
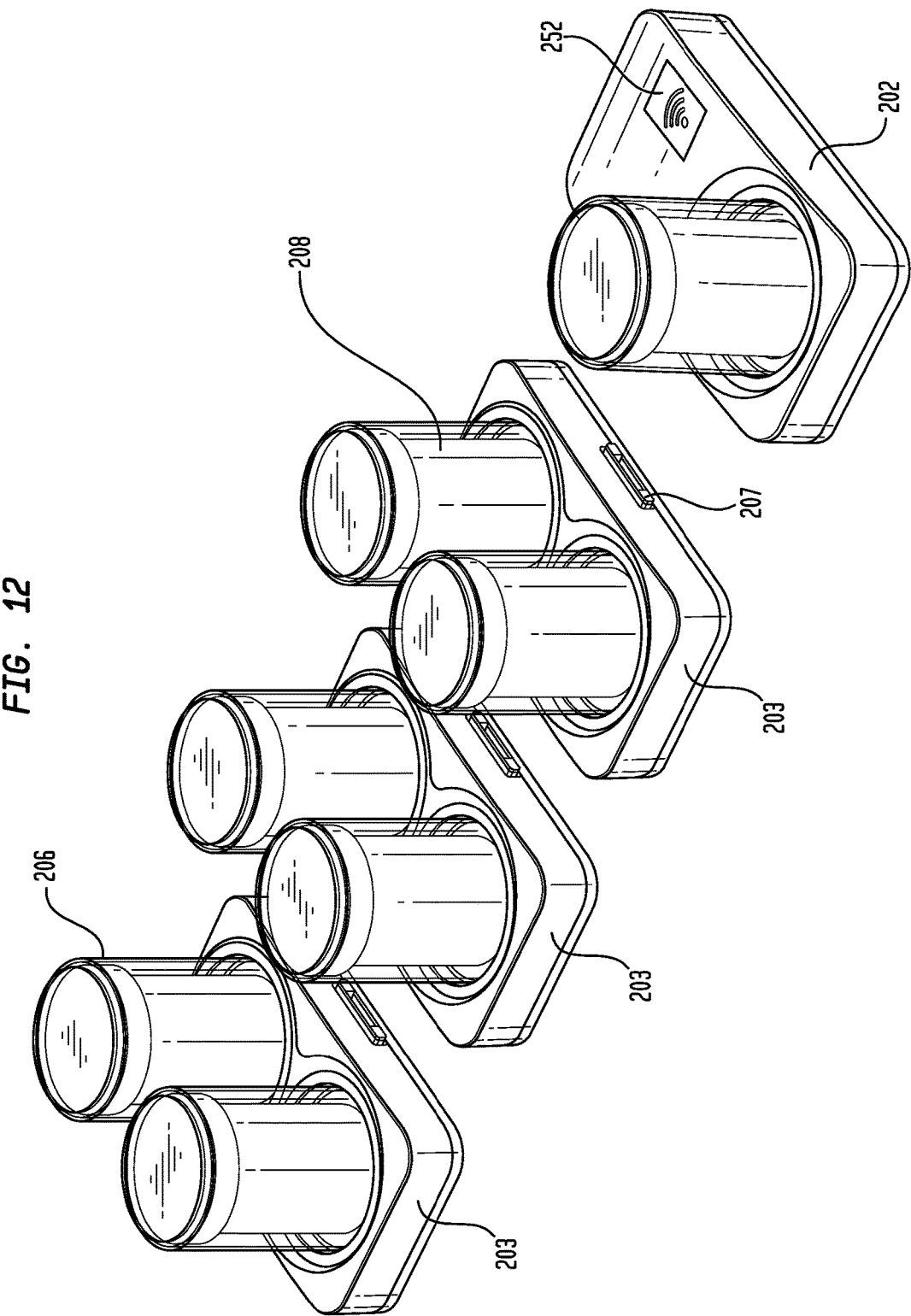
FIG. 12 is an isometric view of some of the elements included in the medicine organizer of FIG. 8 in a modular configuration.
Figure 14:
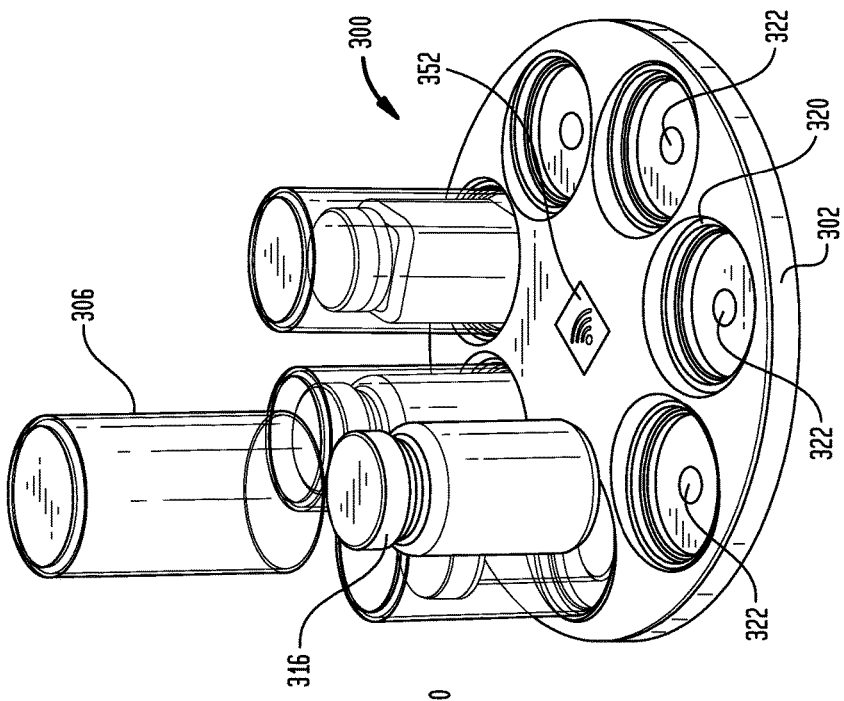
FIG. 14 is an isometric view of some of the elements included in the medicine organizer of FIG. 13 in a modular configuration.
Figure 13:
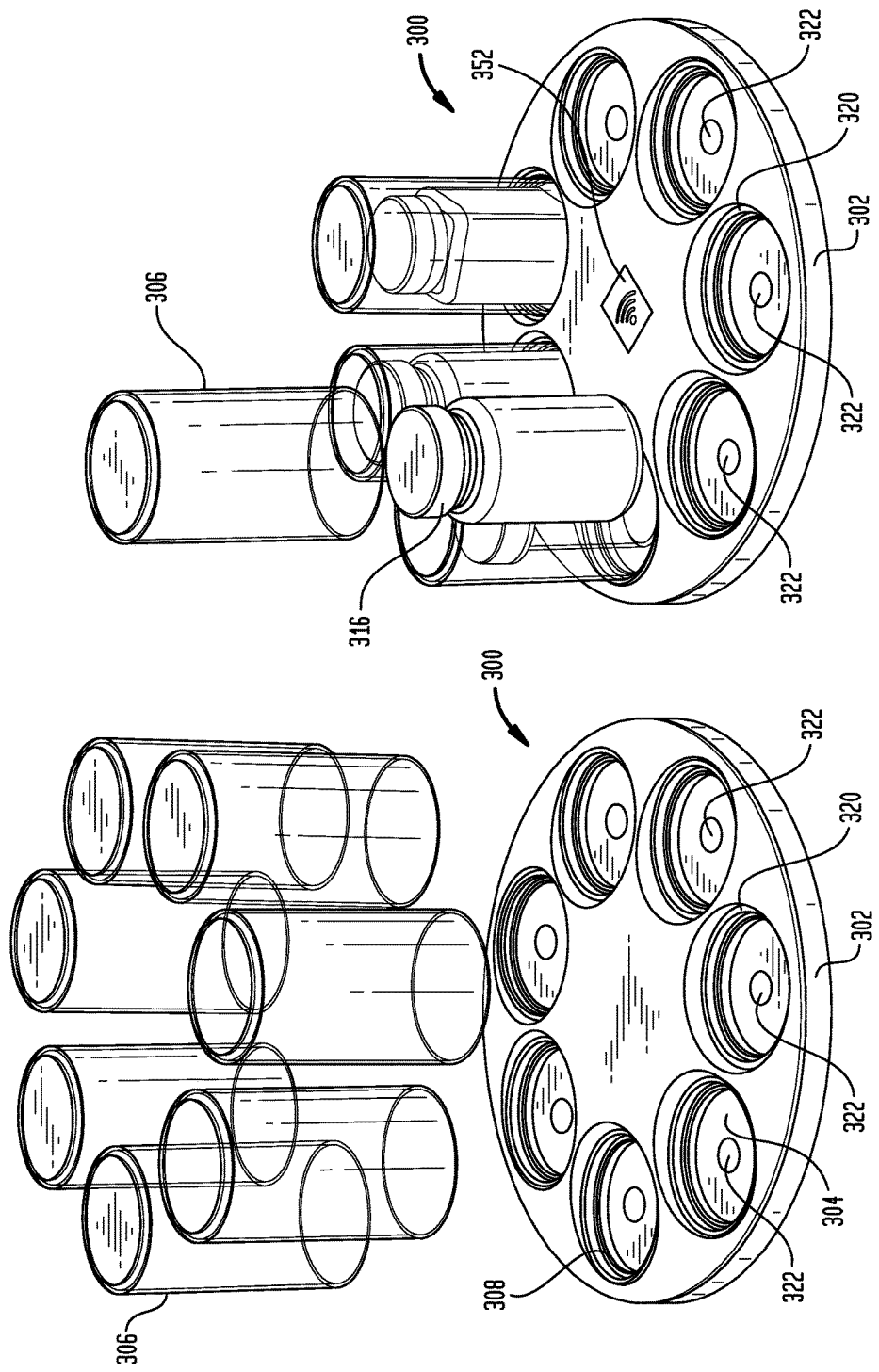
FIG. 13 is an isometric view of a medicine organizer according to another non-limiting embodiment of the present invention.
Figure 17:
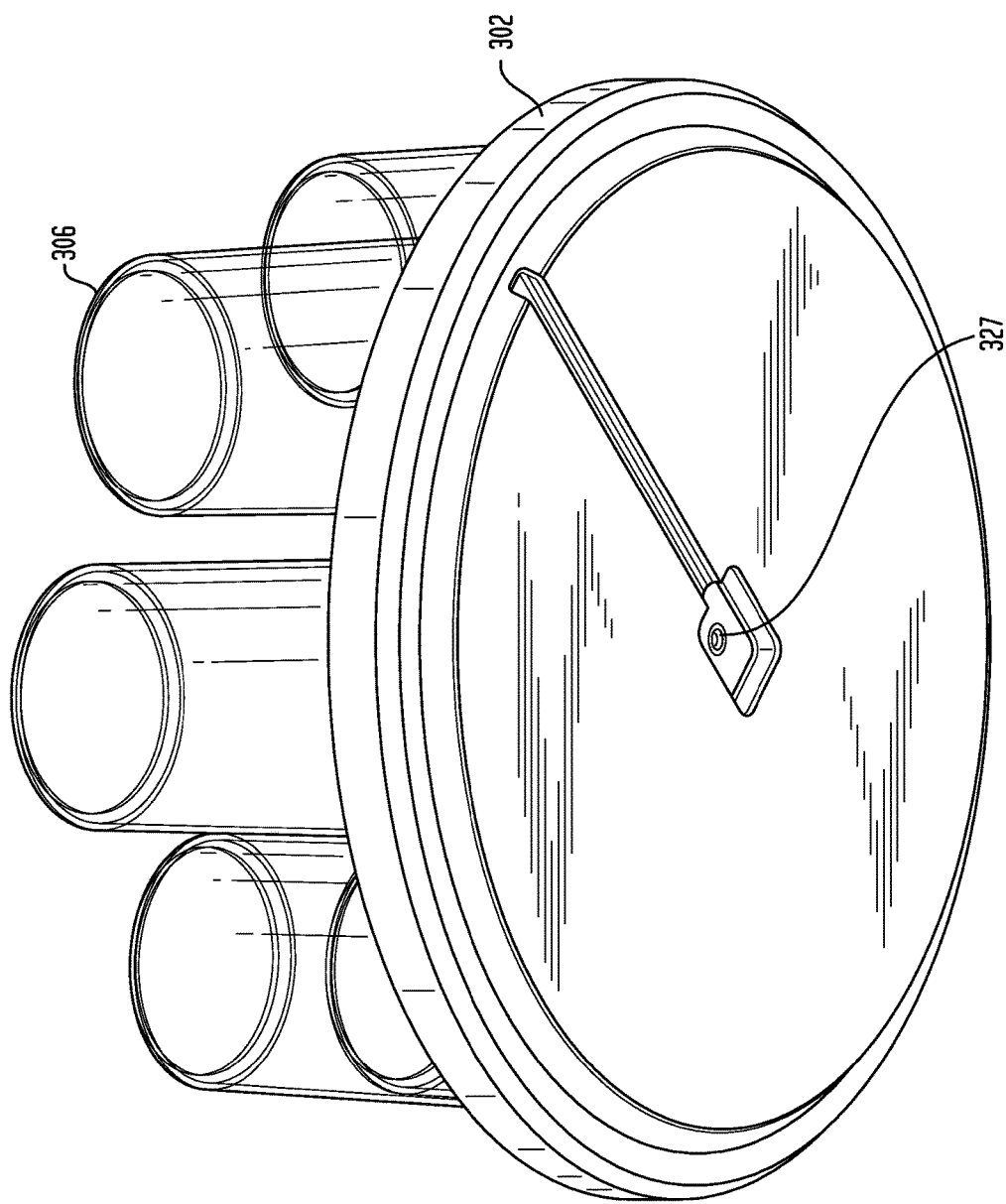
FIG. 17 is an isometric view of some of the elements included in the medicine organizer of FIG. 13 in a modular configuration.
Figure 18A:
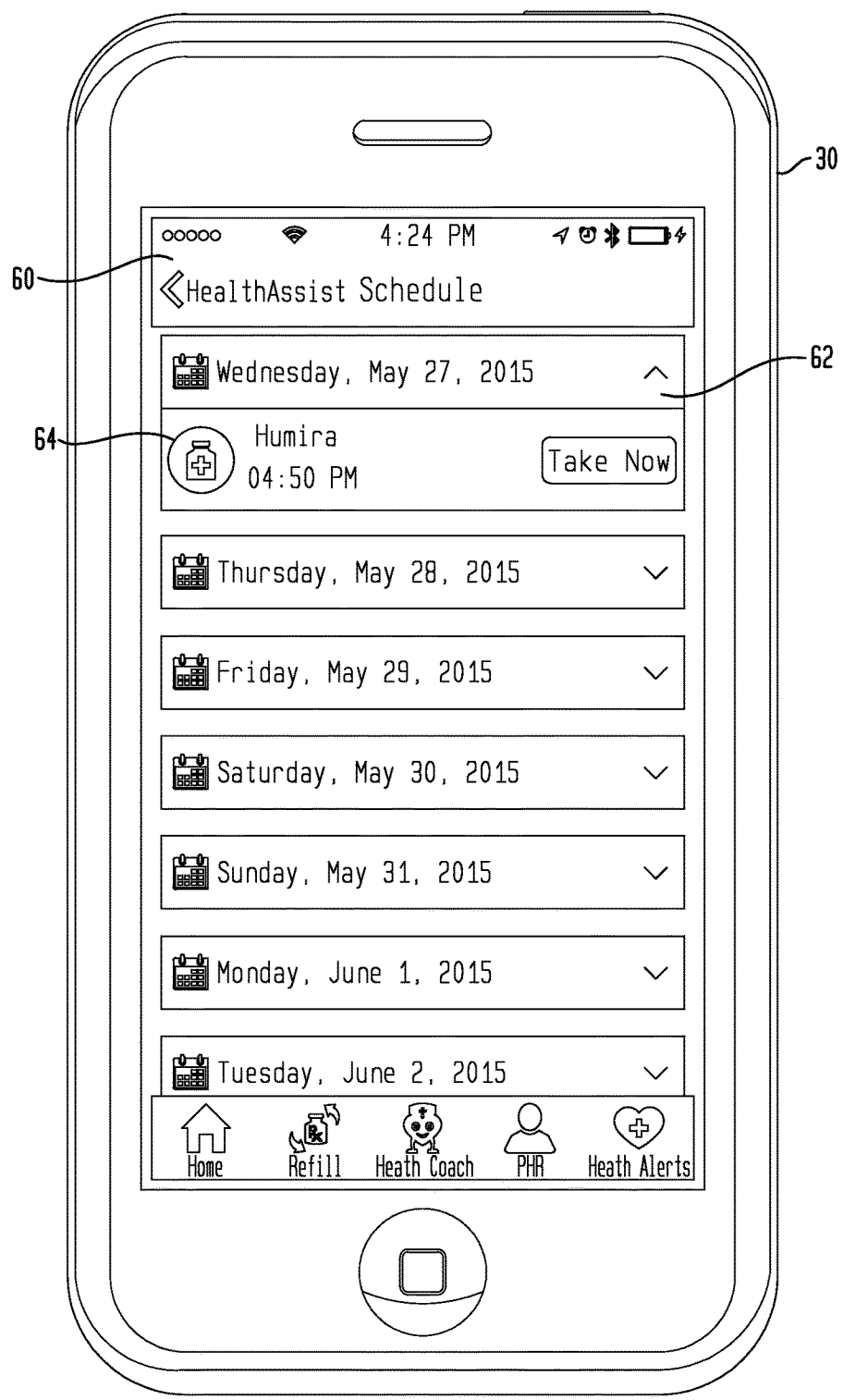
FIG. 18A depicts a medicine schedule screen on a smart device application according to various embodiments of the invention.

For example, referring to FIG. 12, interlocking feature 207, is used to connect an expansion unit housing 203 to the "smart" parent housing 202. Additional expansion housings 203 can be plugged in to each other via the interlocking features (male 207 shown, female not shown) in the housings. As discussed, this modular design allows multiple housings to be daisy chained together wherein the smart end housing provides electronic intelligence and power to the remainder of the units allowing more than one unit to efficiently function as an expandable system. At minimum, the system includes one smart housing and one compartment to store and track medicine use.

In this way, a user can snap one or more "dumb" housings 203 into a "smart" housing 202 in order to provide power, command and control functions to the daisy chain of housings. A user could upgrade a "dumb" medicine holder to be a "smart" medicine holder capable of carrying out the operations discuss above, such as pairing with a smart phone application, automated locking and unlocking, and data collection such as open and closed times or frequency or other desirable functions such as time-temperature limits if a temperature sensor is included.

Once again referring to FIGS. 18A and 18B, the smart device application 60 includes a scheduling screen 62. When a medicine is due, the use will receive a visual or audible prompt 64. As the user approaches the device 200 with the paired smart device, the application can display a reminder screen 66 (FIG. 18B) in order to prompt the user to open the lid 68 or to snooze 70 until a later time when the user wants to take the medicine.

Referring to FIGS. 19A-19C, three example screens for application 60 are shown. Screen 72 depicts an adherence chart indicating the overall patient compliance to the medicine schedule. Screen 74 depicts a schedule screen that shows the user which medicines are due, the time and the date due. Screen 76 depicts the history of when the medicine was taken so that a user may review the prior dosing history.

The user interface has a graphical display designed for ease of use. The user is guided through a series of steps to set up and program the device, dispense medications and perform other desirable functions as described.

In another non-limiting embodiment of the present invention as shown in FIGS. 13-17, device 300 includes a housing 302 having compartments 304 and lids 306 being lockable to the housing to form a closed or an open unit. The device can use a battery to provide power. Alternatively, a hardline power source can also be used. The lids are preferably transparent or translucent.

The housing 302 includes an automated locking mechanism 308 to lock the lid of housing until a medication dose is scheduled to be taken. The locking mechanism is operated by a smart device application as discussed above using a wireless communication protocol and a smart device. When the pre-determined time set in the application occurs, and the smart device is in wireless proximity with a wireless electronic communication module located in the housing (not shown), the housing and the smart device are "paired", thus enabling the lock to open and allow a user access to the medicine via by opening one lid. A signal from the smart phone via a wireless protocol will enable a mechanical device such as a solenoid, actuator or magnet to open or close the lock (not shown). A person of ordinary skill in the electro-mechanical arts will understand that the proximity locking and unlocking function can be carried out in a number of known ways.

The housing includes compartments 302 for storing medicine vials 316. The compartments can include a light 320 for each compartment, such as, for example an LED light, or an illuminated area which can illuminate, change color, or flash when it is time to take a medication stored inside the compartment, when the device malfunctions, when the device is paired to a smart phone, or when the device is low on power.

In some embodiments, the housing can include a by-pass switch to allow a user to unlock the lid in case of emergency or malfunction and to allow access to the contents of the housing. The use of the by-pass switch can be electronically recorded and sent to the smart phone application for review and analysis.

In this embodiment, each compartment includes a switch or sensor 322 for sensing when the lid is opened or closed. The sensors can be, for example, an electrical switch, a mechanical switch, or an optical switch or other sensor.

The housing 302 also includes a wireless transceiver 352 or chip set and associated hardware necessary to carry out the wireless command and control function and to communicate information to the smart device and the application residing on the device. Information regarding the status of the lid, including when it is opened and closed, or how many times it opened or closed, can be transmitted to the smart device and utilized by the application to provide user data.

In this embodiment, sensors 322 located within the compartments can be used to sense when a vial is in a compartment. The sensor can send position data via the wireless connection protocol to the smart device which can be utilized by the application to provide user data. Designated compartments will illuminate when it is time to take this medicine stored in the corresponding compartment. Once a vial is removed from a compartment, the illumination with automatically shut off after the vial has been removed and replaced into its compartment. After dosing, when each vial is replaced in the device, the lid is replaced and locked and the dosing program continues according to the preprogrammed application.

In use, a user installs custom software application on a smart device such as smart phone 30. After the application "pairs" the smart device with wireless chip set or wireless transceiver, the lock can be disengaged and the user can open the lid.

Next, the user can load medicine vials or other medicines into the compartments of the housing and close the lids to lock the contents inside the housing and start a dosing regimen.

In this embodiment, the application can be programmed to send the user an alarm on the smart phone and illuminate the light(s) in the appropriate compartments at pre-determined times.

When the user next approaches the device, (i.e. the smart device and housing will remain "paired" and will connect wirelessly when the phone is in range of the housing) the smart phone application can be used to open the locking mechanism by sending a wireless signal to actuate the locking mechanism. The user can now access the medicine vials stored in the device.

In some embodiments, the locking mechanism can include a an independent locking system for each compartment and corresponding lid such that a vial placed in a compartment by a user can be electronically locked or unlocked in the compartment according to a dosing schedule. Preferably a corresponding illumination and de-illumination of the associated light alerts a user to see which compart or vial is unlocked to access the medicine at the appropriate time Alternately, a central locking mechanism can be use such that a lock controller can rotate within the housing to the appropriate position in order to unlock the compartment and lid containing the medicine vial(s) at the predetermined times(s).

When the user accesses the medicine, a sensor can electronically time stamp each time the lid is opened or closed. This data can be sent to the smart phone application for review and analysis. After each use, the lid is closed and locked. A timer in the application restarted so that when the next dose is due, the process is repeated.

It is envisioned that the control system can be programmed to allow only one compartment and lid to be unlocked at a given time. This feature is designed for safety. That is, one compartment at a time is illuminated and unlocked. The user takes the medicine, returns the vial and replaces the lid. The light is extinguished and the compartment is locked. The process is repeated with the next medicine of interest. In this way, the user must replace the vial in the proper compartment thereby preventing unauthorized use or misuse of the correct medicine and ensuring compliance with the pre-programmed dosing schedule for one or more medicines. It will be understood by a person of ordinary skill in the mechanical arts that the components for a locking mechanism of either configuration can be constructed from known materials using standard manufacturing methods.

Referring to FIGS. 18A-18B and 19A-19C, in one embodiment, the smart device application 60 includes a scheduling screen 62. When a medicine is due, the user will receive a visual or audible prompt 64. As the user approaches the device 100 with the paired smartphone, the application can display a reminder screen 66 (FIG. 8B) in order to prompt the user to open 68 the lid or to snooze 70 until a later time when the user wants to take the medicine.

Referring to FIGS. 19A-19C, three example screens of application 60 are shown. Screen 72 depicts an adherence chart indicating the overall patient compliance to the medicine schedule. Screen 74 depicts a schedule screen that shows the user which medicines are due, the time and the date due. Screen 76 depicts the history of when the medicine was taken so that a user may review the prior dosing history.

In some embodiments, the housing can include a battery or a rechargeable battery. Optionally, the housing can be powered by an external power source, through power port 327 (See FIG. 17), such as by a plug and power outlet and can include a backup battery in case of power failure.

EXAMPLES

In use, a doctor can explain to a patient that medication will be necessary to effectively treat the patient's condition.

A medication schedule, specifying dose and frequency can be provided to the patient. Once the schedule is determined, the clinical nurse educator or the patient's pharmacist, or the patient can program an application that resides on a smart phone or other device with the details of the patient's medication schedule.

For example, the patient may be required to take three pills three times each week, on Monday mornings at 10:00 am.

In practice, on Monday morning at 10:00 am each week the smart device will sound an alarm reminding the patient that one or more medicines are scheduled. Unlike other applications that merely provide alarm reminders, the instant alarm can only be turned off by opening the proper lid of the device.

If the time is inconvenient for the patient, the patient can interact with a prompt to the question, for example, "Do you want to administer your injection now?" to "snooze" the alarm.

Once the appropriate lid or lids where the scheduled medicine is stored is opened, a sensor sends a signal via the wireless antenna to the smart phone application, which in turn can send a message, for example an e-mail or a text message, to the patient's caretaker or health care professional.

After the device is programmed and loaded, the smart phone will alert the user when it is time to take the appropriate medication. First, the smart phone signals the user with a visual or audible alarm or both. The audible alarm can be selected from the audio files residing on the phone. For example, a ring tone or a song may act as an audible alarm. At the same time, the phone screen can display a visual alert including the dose time, an image of the pills to be taken and their names.

To dispense the medication, the smart device is paired to the wireless electronics located in the housing. A wireless signal from the device unlocks the lid of the appropriate compartment. The user can open the lid to access the proper medicine at the proper time.

The smart device will enter an alert mode when a dose is missed. The screen will display which medications were missed along with the dose time and images of the missed medications. Further, the application can provide useful instructions to the user regarding what to do in the event of a missed dose and provides instant access to the prescribing doctor's phone number. With a single touch of the phone touch screen, the patient can call the prescribing doctor for additional advice. The smart device can also provide internet hyperlinks to the medicine manufacturer's website for additional information about each medication.

When the lid is opened and the medicine is accessed, a signal can be sent from the smart device via a wireless network to a user's private database. The database can be maintained on the phone and on a secure server. The database can be synchronized. The network can be a cell phone network, a Wi-Fi network or any other type of wireless network.

In one embodiment, the application may include the ability to communicate through a hard line network such as a cable network or fiber optics network to connect to the internet.

Dispensing data can be communicated to a remote server database; the data is available for review by the user or a care taker. The data may be presented in any number of ways including charts, graphs or tables. In this way, the user's medication dispensing history can be reviewed for compliance with the desired schedule for taking medications.

In one embodiment, the application includes a feature which alerts a care taker that a dose has not been dispensed via a wireless network. For example, application generates a phone message, text message or e-mail message which is sent directly to the user, care taker, doctor or any number of interested parties. This feature can be particularly useful when, for example, a care taker or family member desires to monitor the medication dispensing compliance of a senior citizen such as a parent or family member or individual who may be suffering from a memory disorder or who may simply be forgetful. When the user receives a "missed dose" message, appropriate action can be taken in real-time to correct the short term non-compliance and address the longer term issues associated with the inability or unwillingness of a patient to comply with a medication schedule.

As illustrated above, users can input data for numerous medications into the smart phone application. Medication specific supplementary information can also be provided directly by the manufacturer for one or more medications. Supplementary information can include, for example, the name of the medication, its function, how and when the medication should be taken, missed dose information, information about side effects including specific actions required if the patient experiences side effects, possible interactions with other medications, and where the patient can find additional information about the medication, such as hyperlinks to the manufacturer's website. Further, manufacturers can send coupons and other desirable information such as, for example, safety alerts directly to users through the wireless network.

The smart phone includes a software application that is programmed to store a medicine and schedule data for one or more medications. The phone database stores medicine and schedule information that is input by the user or acquired from the manufacture's database. The phone database can be used to command the locking lid or drawer locks to locked or unlocked positions. When a dose is dispensed or missed by the user, the phone communicates with the secure server database. The server database can be accessed by users having a password and a username. Authorized users can login to the database to monitor patient compliance.

It is contemplated that numerous graphs and reports can be displayed or printed such that the person accessing the database can easily recognize compliance problems, determine whether there are any recurring compliance problems, or print medication lists.

As previously described, the database can communicate with a monitoring module. In the event of a compliance problem, for example, a missed dose of heart medication, the module can issue commands to send an alarm or alarms to concerned individuals by e-mail, text or other means. In this way, a care taker can be timely notified of a missed dose and can implement corrective action.

As will also be appreciated, a significant benefit of the present invention includes the ability to store the user's medicine schedule on a smart phone which the user may carry with them. A patient's medication information can be invaluable to a new doctor or in the event a user is taken to the hospital. The present invention allows a nurse, doctor, EMT or other health care professional to access a patient's medication regimen or dispensing history by accessing a smart phone or a server database. This feature can dramatically reduce the risk of prescribing the wrong medication and also reduce the time before necessary treatment is administered.

Although the invention herein has been described with reference to particular embodiments, it is to be understood that these embodiments are merely illustrative embodiments and that other arrangements may be devised without departing from the spirit and scope of the present invention as defined by the disclosure herein.

What is claimed is:
1. An apparatus comprising:
   (a) a first smart module including a housing, a smart end cap, and at least one compartment configured for storing a medicine vial, said module including a lockable lid;
   (b) at least one infrared or optical sensor, said at least once sensor being located within said housing, said at least one sensor being configured to remotely detect the presence or the absence of said medicine vial in said at least one compartment;
   (c) at least one light, said at least one light, wherein said at least one light is capable of being commanded to an illuminated condition to illuminate said at least one compartment at a predetermined medication time;
   (d) a wireless controller, said controller being connected to a smart end cap, said controller being capable of opening and locking said lockable lid and illuminating said at least one light, wherein said wireless controller utilizes a BLUETOOTH™ wireless protocol for pairing with a smart device;
   (e) a smart device, wherein said smart device is a smart phone or tablet, said device being capable of commanding said controller to open said lid and illuminate said at least one light at said predetermined medication time, wherein said smart device executes a software application for alerting a user at said predetermined medication time based on a data set input by said user, wherein said data set includes a name of a medicine, a strength of said medicine, and a time for dispensing said medicine; and
   (f) a plurality of separate dumb modules, said plurality of modules being configured to be assembled together and electrically interconnected with each other and said first module, wherein said wireless controller is connected to said smart end cap for locking or unlocking a lid and illuminating a light in each of said plurality of modules.

2. The apparatus of claim 1, wherein said at least one light is an LED.

3. A method for administration of medicine comprising:
   a. entering a predetermined medication time into a smart wireless device executing a software application;
   b. sending a wireless signal from said smart wireless device to a module including a smart end cap, thereby commanding a lid to an unlocked position;
   c. loading a medicine vial into a compartment, said compartment including a light;
   d. sending a wireless signal from said smart wireless device to a module including a smart end cap, thereby commanding said lid to a locked position; and
   e. generating an alert from said smart wireless device at said predetermined medication time, said alert including a visual or audible alarm;
   f. sending a wireless signal from said smart wireless device to a module including a smart end cap to command said lid to an unlocked position and said light to an illuminated condition, thereby alerting a user that it is time to take said medicine and indicating the location of said medicine.

4. The method of claim 3, further comprising the step of transmitting a wireless signal from said smart device to a remote database, said signal indicating either a confirmation of dispensing said medicine or a failure to dispense said medicine.

5. The method of claim 3, further comprising the step of transmitting one or more alarms via a wireless signal from said smart device when said medicine is not dispensed within a predetermined time of said predetermined medication time.

6. The method of claim 3 further comprising the step of sending a wireless signal from said smart device to a remote database when a user attempts to dispense said medicine before a predetermined time.

* * * * *